United States Patent
Roman

(10) Patent No.: US 9,895,179 B2
(45) Date of Patent: *Feb. 20, 2018

(54) INTRAMEDULLARY FIXATION DEVICES

(71) Applicant: Arrowhead Medical Device Technologies, LLC, Collierville, TN (US)

(72) Inventor: Scott Richard Roman, Hampton, GA (US)

(73) Assignee: Arrowhead Medical Device Technologies, LLC, Collierville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,329

(22) Filed: Apr. 21, 2017

(65) Prior Publication Data

US 2017/0215929 A1 Aug. 3, 2017

Related U.S. Application Data

(60) Continuation of application No. 14/514,711, filed on Oct. 15, 2014, now Pat. No. 9,629,671, which is a continuation of application No. 14/162,226, filed on Jan. 23, 2014, now Pat. No. 8,888,778, which is a division of application No. 13/084,048, filed on Apr. 11, 2011, now Pat. No. 8,685,024.

(60) Provisional application No. 61/324,080, filed on Apr. 14, 2010.

(51) Int. Cl.
*A61B 17/72* (2006.01)
*A61B 17/16* (2006.01)

(52) U.S. Cl.
CPC .......... *A61B 17/7291* (2013.01); *A61B 17/16* (2013.01); *A61B 17/7225* (2013.01); *A61B 17/7233* (2013.01)

(58) Field of Classification Search
CPC ............ A61B 17/7291; A61B 17/7225; A61B 17/7233
USPC ........................ 606/62–68; 623/22.19, 21.15
See application file for complete search history.

(56) References Cited

U.S. PATENT DOCUMENTS

| | | |
|---|---|---|
| 3,593,342 A | 7/1971 | Niebauer et al. |
| 3,646,615 A | 3/1972 | Ness |
| 3,681,786 A | 8/1972 | Lynch |

(Continued)

FOREIGN PATENT DOCUMENTS

| | | |
|---|---|---|
| DE | 19813914 | 9/1999 |
| DE | 20212359 | 11/2002 |

(Continued)

OTHER PUBLICATIONS

International Searching Authority/United States Patent Office, "International Search Report" for PCT/US2011/032057, dated Jul. 5, 2011, 2 pages.

(Continued)

*Primary Examiner* — Pedro Philogene
*Assistant Examiner* — David C Comstock
(74) *Attorney, Agent, or Firm* — Heslin Rothenberg Farley & Mesiti P.C.

(57) ABSTRACT

An internal intramedullary fixation device for the stabilization of bone in arthrodesis and fractures of the foot and hand is disclosed. During implantation in the medullary canal of each bone, the device grasps the edges of the canal, stabilizing the bone (internally) during the natural healing process.

20 Claims, 6 Drawing Sheets

(56) References Cited

U.S. PATENT DOCUMENTS

| | | | |
|---|---|---|---|
| 3,875,594 A * | 4/1975 | Swanson | A61F 2/4241 |
| | | | 623/18.11 |
| 4,262,665 A | 4/1981 | Roalstad et al. | |
| 4,304,011 A | 12/1981 | Whelan, III | |
| 4,516,569 A | 5/1985 | Evans et al. | |
| 4,549,319 A | 10/1985 | Meyer | |
| 4,667,663 A | 5/1987 | Miyata | |
| 4,704,686 A | 11/1987 | Aldinger | |
| 4,873,976 A | 10/1989 | Schreiber | |
| 4,884,572 A | 12/1989 | Bays et al. | |
| 4,898,186 A | 2/1990 | Ikada et al. | |
| 4,976,715 A | 12/1990 | Bays et al. | |
| 5,047,059 A | 9/1991 | Saffar | |
| 5,053,035 A | 10/1991 | McLaren | |
| 5,171,284 A | 12/1992 | Branemark | |
| 5,201,735 A | 4/1993 | Chapman et al. | |
| 5,203,864 A | 4/1993 | Phillips | |
| 5,236,431 A | 8/1993 | Gogolewski et al. | |
| 5,391,181 A | 2/1995 | Johnson et al. | |
| 5,425,777 A | 6/1995 | Sarkisian et al. | |
| 5,474,557 A | 12/1995 | Mai | |
| 5,480,447 A | 1/1996 | Skiba | |
| 5,667,510 A | 9/1997 | Combs | |
| 5,669,912 A | 9/1997 | Spetzler | |
| 5,824,095 A | 10/1998 | Di Maio, Jr. et al. | |
| 5,893,850 A | 4/1999 | Cachia | |
| 5,919,193 A | 7/1999 | Slavitt | |
| 5,984,971 A | 11/1999 | Faccioli et al. | |
| 5,993,475 A | 11/1999 | Lin et al. | |
| 6,319,284 B1 | 11/2001 | Rushdy et al. | |
| 6,352,560 B1 | 3/2002 | Poeschmann et al. | |
| 6,689,169 B2 | 2/2004 | Harris | |
| 6,692,499 B2 | 2/2004 | Tormala et al. | |
| 6,736,818 B2 | 5/2004 | Perren et al. | |
| 6,811,568 B2 | 11/2004 | Minamikawa | |
| 7,025,789 B2 | 4/2006 | Chow et al. | |
| 7,041,106 B1 | 5/2006 | Carver et al. | |
| 7,918,879 B2 | 4/2011 | Yeung et al. | |
| 8,100,983 B2 | 1/2012 | Schulte | |
| 8,202,306 B2 | 6/2012 | Dreyfuss | |
| 8,328,806 B2 | 12/2012 | Tyber et al. | |
| 8,337,537 B2 | 12/2012 | Pelo et al. | |
| 8,357,162 B2 | 1/2013 | Frake | |
| 8,414,583 B2 | 4/2013 | Prandi et al. | |
| 8,475,456 B2 | 7/2013 | Augoyard et al. | |
| 8,672,986 B2 | 3/2014 | Klaus et al. | |
| 8,685,024 B2 * | 4/2014 | Roman | A61B 17/7225 |
| | | | 606/62 |
| 8,696,716 B2 | 4/2014 | Kartalian et al. | |
| 8,715,325 B2 | 5/2014 | Weiner et al. | |
| 9,629,671 B2 * | 4/2017 | Roman | A61B 17/7291 |
| 2002/0082705 A1 | 6/2002 | Bouman et al. | |
| 2007/0243225 A1 | 10/2007 | McKay | |
| 2008/0195219 A1 | 8/2008 | Wiley et al. | |
| 2008/0221597 A1 | 9/2008 | Graser | |
| 2011/0118739 A1 | 5/2011 | Tyber et al. | |
| 2011/0257755 A1 | 10/2011 | Bellemere et al. | |
| 2011/0301652 A1 | 12/2011 | Reed et al. | |
| 2012/0089197 A1 | 4/2012 | Anderson | |
| 2013/0172889 A1 | 7/2013 | Tyber et al. | |

FOREIGN PATENT DOCUMENTS

| | | |
|---|---|---|
| DE | 10134511 | 2/2003 |
| DE | 20218993 | 2/2003 |
| EP | 1870050 | 12/2007 |
| FR | 2846545 | 5/2004 |
| GB | 2430625 | 4/2007 |
| JP | 56-144512 | 10/1981 |
| WO | WO 03/007839 | 1/2003 |
| WO | WO-2005063149 | 7/2005 |
| WO | WO-2006099886 | 9/2006 |
| WO | WO 2011130229 | 10/2011 |

OTHER PUBLICATIONS

SmartToe Intramedullary Shape memory Implant, product Information, Memometal, Inc., 2009, 2 pages.

Pro-Toe™ VO hammertoe Fixation System, Surgical Technique, FA196-410R311, Wright Medical Technology, Inc., 2011, 12 pages.

Crenshaw, A. H., ed., "Campbell's Operative Orthopaedics, vol. 2," 7th edition, The C.V. Mosby Company, Washington DC, 1987, p. 937-945, cover and copyright pages, 11 pages.

International Search Report and Written Opinion issued for PCT/US2014/022058, dated Jun. 25, 2014, 15 pages.

Supplementary European Search Report issued for EP 11769413 dated May 6, 2014, 6 pages.

International Search Report and Written Opinion issued for PCT/US2014/024599, dated Aug. 6, 2014, 11 pages.

International Search Report and Written Opinion Issued for PCT/US2014/024485, dated Jul. 10, 2014, 17 pages.

International Search Report and Written Opinion Issued for PCT/US2014/022058, dated Juno 25, 2014, 15 pages.

\* cited by examiner

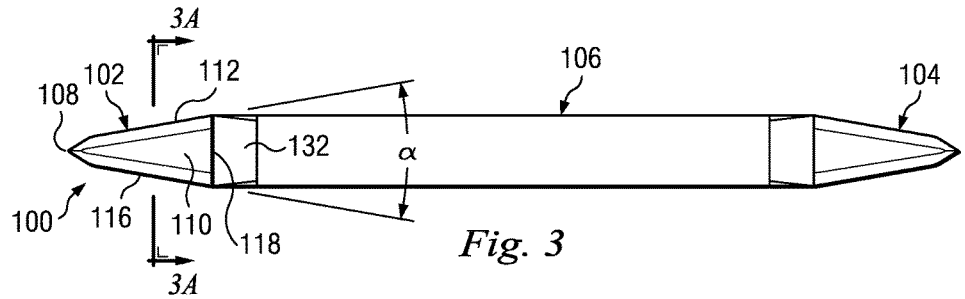
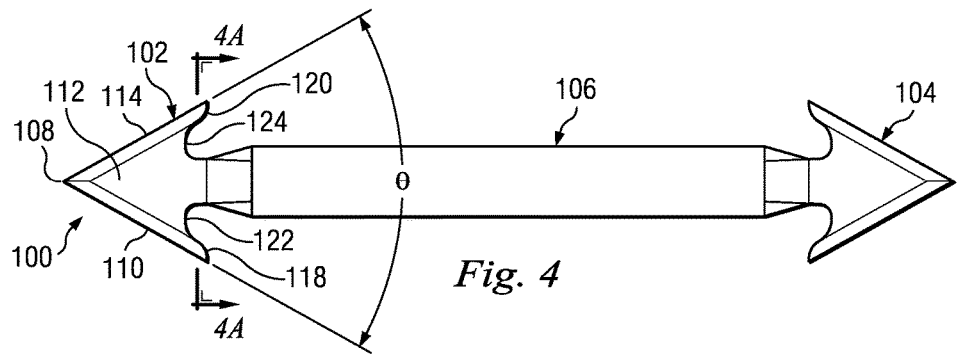
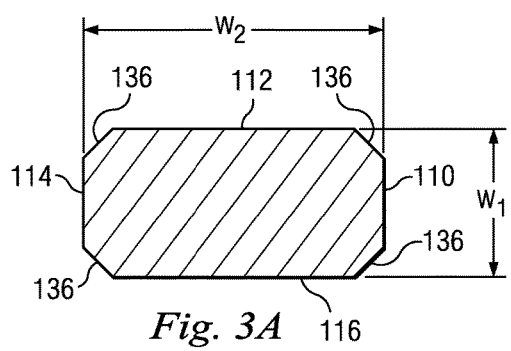
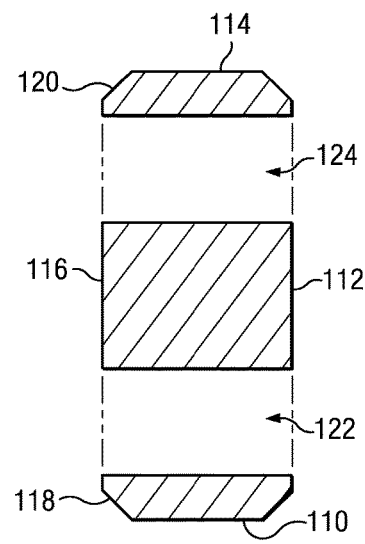

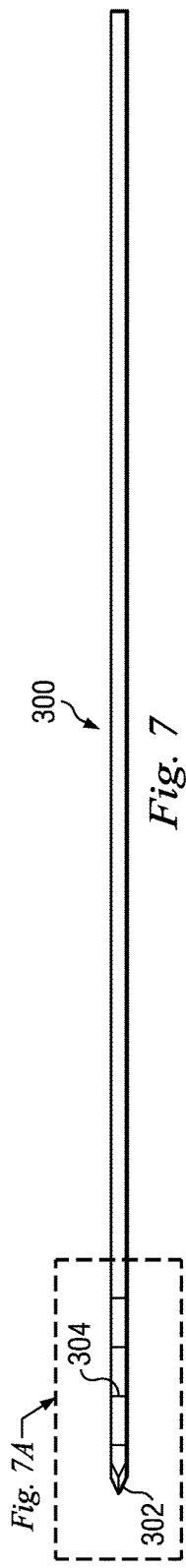
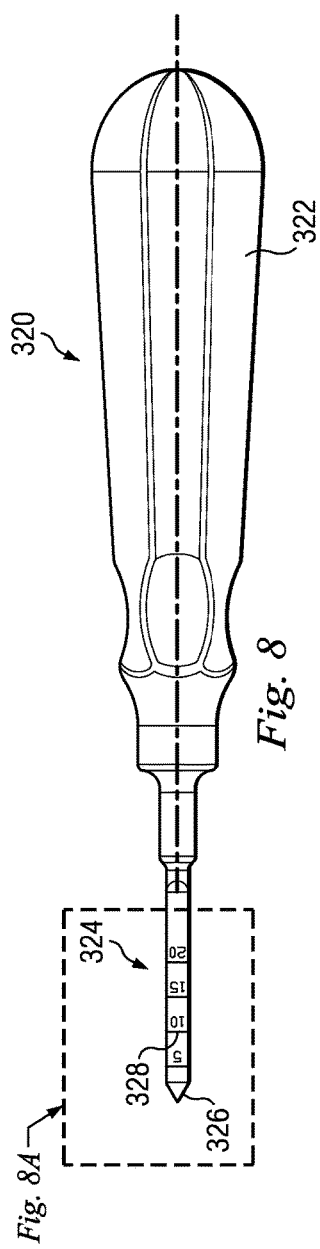
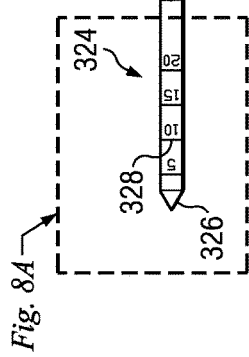
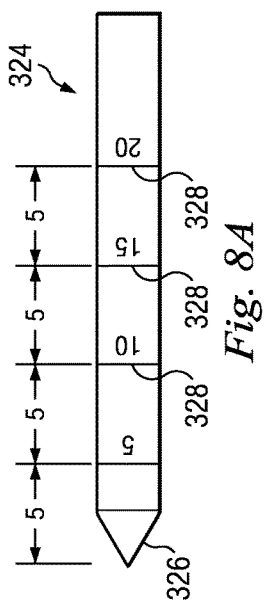
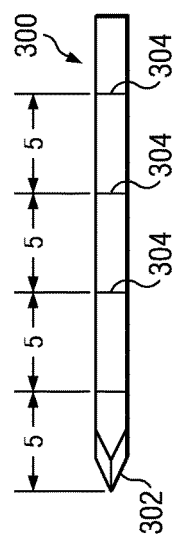

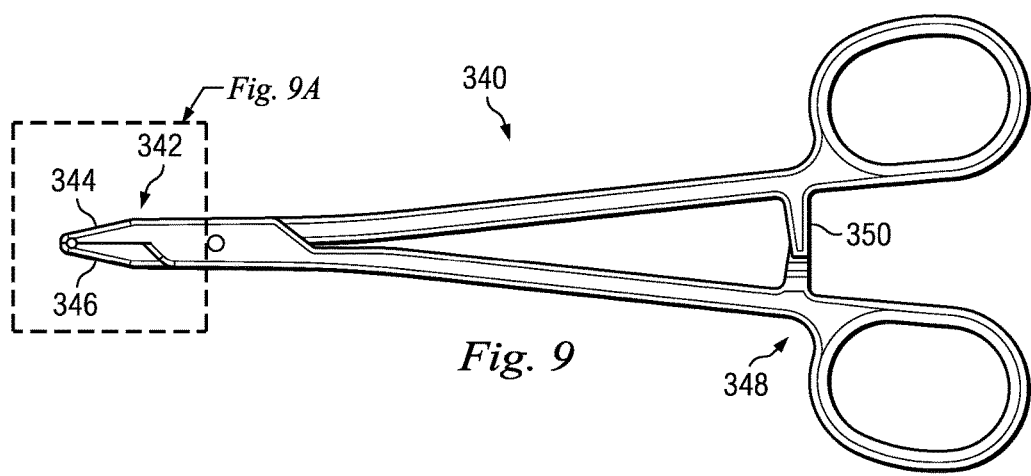
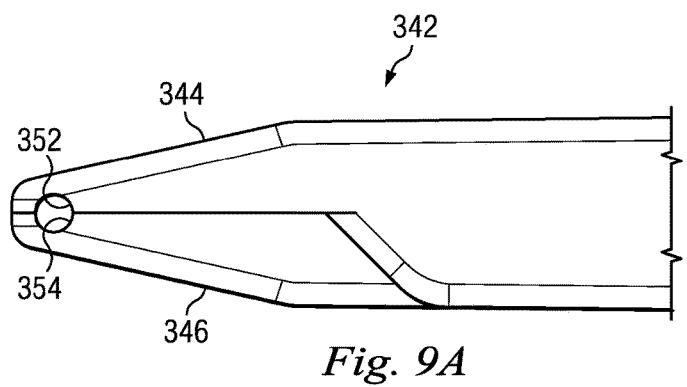

INTRAMEDULLARY FIXATION DEVICES

CROSS-REFERENCE TO RELATED APPLICATIONS

The present application is a continuation application of U.S. patent application Ser. No. 14/514,711, filed on Oct. 15, 2014, entitled "Intramedullary Fixation Device and Methods for Bone Fixation and Stabilization," which is a continuation application of U.S. patent application Ser. No. 14/162,226, filed on Jan. 23, 2014, entitled "Intramedullary Fixation Device and Methods for Bone Fixation and Stabilization", which is a divisional application of U.S. patent application Ser. No. 13/084,048, filed on Apr. 11, 2011, entitled "Intramedullary Fixation Device and Methods for Bone Fixation and Stabilization", now U.S. Pat. No. 8,685,024 issued Apr. 1, 2014 and claims the benefit of U.S. Provisional Application No. 61/324,080, entitled "The Arrowhead Fixation Device is an Intramedullary Fixation Device Used in Bone Fixation and Stabilization," filed Apr. 14, 2010, each of which are incorporated herein by reference.

BACKGROUND

Hammertoe deformities occur when the metatarsophalangeal joint between phalanges in a toe are cocked upward and the proximal interphalangeal joint bends downward. This deformity can become quite painful and can limit the ability of a person with hammertoe to walk and perform other daily activities. Hammertoe may be caused by any number of factors, including the long-term use of poorly fitting shoes, having a long second toe, hallux valgus pressing against the second toe, connective tissue disorders and trauma.

While some minor cases may be treated with non-surgical remedies, surgeries are often necessary to provide real correction and pain relief. Some surgical methods include stabilizing the toes using a smooth K-wire placed in an antegrade manner through the middle and distal phalanges while joint extension and distraction are maintained. The K-wire may then be placed in retrograde fashion into the proximal phalanx while joint extension and distraction are maintained. Fixation lasts for 4-6 weeks after surgery. During that time, the pins are capped so that the sharp ends do not catch on objects, such as bed sheets. Even with this form of fixation, non-unions, K-wire migration, and loss of fixation can be quite common. Further, the external K-wires may lead to pin tract infections or movement of bone along the smooth wire, including rotation of the distal aspect of the toe. These types of challenges make alternative fixation methods desirable.

The devices and methods disclosed herein overcome one or more of the problems in the prior art.

SUMMARY

In one exemplary aspect, the present disclosure is directed to an intramedullary fixation device used in bone fixation and stabilization. The device may include an arrowhead-shaped distal head comprising a distal end having a sharp point and comprising first, second, third, and fourth outwardly facing side surfaces forming a pyramidal shape. The first and third side surfaces may be opposed from each other and may form a first angle, and the second and fourth side surfaces may be opposed from each other and may form a second angle. The second angle may be different than the first angle. Each of the first and third side surfaces may have a proximally projecting edge forming a tip of a barb. The barbs may be configured to engage tissue and inhibit rotational movement and inhibit axial movement of the distal head in a proximal direction. The device may also include an arrowhead-shaped proximal head comprising a proximal end having a sharp point and comprising fifth, sixth, seventh, and eighth outwardly facing side surfaces. The fifth and seventh side surfaces may be opposed from each other and may form a third angle. The sixth and eighth side surfaces may be opposed from each other and may form a fourth angle, with the third angle being different than the fourth angle. Each of the fifth and seventh side surfaces may have a distally projecting edge forming a tip of a barb. The barbs may be configured to engage tissue and inhibit rotational movement and inhibit axial movement of the proximal head in a distal direction. A rigid body extends between and connects the distal head and the proximal head. The body may have a rigidity sufficient to withstand bending loading applied by the phalanges.

In another exemplary aspect, the present disclosure is directed to an intramedullary fixation device used in bone fixation and stabilization. The device may include an arrowhead-shaped distal head having first, second, third, and fourth outwardly facing side surfaces forming a pyramidal shape. The first and third side surfaces may be opposed from each other and may form a first angle, and the second and fourth side surfaces may be opposed from each other and may form a second angle. Each of the first and third side surfaces may have a proximally projecting edge forming a tip of a barb. The barbs being configured to engage tissue and inhibit movement of the distal head in a proximal direction. The second and fourth side surfaces lack proximal edges forming barbs. The device may also include an arrowhead-shaped proximal head having fifth, sixth, seventh, and eighth outwardly facing side surfaces. The fifth and seventh side surfaces may be opposed from each other and may form a third angle, and the sixth and eighth side surfaces may be opposed from each other and may form a fourth angle. Each of the fifth and seventh side surfaces may have a distally projecting edge forming a tip of a barb. The barbs may be configured to engage tissue and inhibit movement of the proximal head in a distal direction. The sixth and eighth side surfaces may lack proximal edges forming barbs. The device also may include a cylindrical body extending between and connecting the distal head and the proximal head. The cylindrical body may have a rigidity sufficient to withstand bending loading applied by the phalanges.

In another exemplary aspect, the present disclosure is directed to an intramedullary fixation device used in bone fixation and stabilization. The device may include an arrowhead-shaped distal head comprising a distal end having a sharp point and comprising first, second, third, and fourth outwardly facing side surfaces forming a pyramidal shape. The first and third side surfaces may be opposed from each other and may form a first angle, and the second and fourth side surfaces may be opposed from each other and may form a second angle, with the second angle being different than the first angle. Each of the first and third side surfaces may have a proximally projecting edge forming a tip of a barb. The distal head also may include a first undercut and a second undercut, where each of the first and second undercuts have a depth such that the barb tips are disposed proximal of the respective undercut. The barbs may be configured to engage tissue and inhibit movement of the distal head in a proximal direction. The derive may also include an arrowhead-shaped proximal head comprising a proximal end having a sharp point and comprising fifth, sixth, seventh, and eighth outwardly facing side surfaces.

The fifth and seventh side surfaces may be opposed from each other and may form a third angle, and the sixth and eighth side surfaces may be opposed from each other and may form a fourth angle, with the third angle being different than the fourth angle. Each of the fifth and seventh side surfaces may have a distally projecting edge forming a tip of a barb. The proximal head also may comprise a third undercut and a fourth undercut. Each of the third and fourth undercuts may have a depth such that the barb tips are disposed distal of the respective undercut. The barbs may be configured to engage tissue and inhibit movement of the proximal head in a distal direction. A rigid body extends between and connects the distal head and the proximal head. The body may have a rigidity sufficient to withstand bending loading applied by the phalanges. It may comprise a main portion, a distal neck portion, and a proximal neck portion. The distal and proximal neck portions may have a cross-sectional area smaller than a cross-section area of the main portion. The distal neck portion may support the distal head and the proximal neck portion may support the proximal head. The distal neck may intersect with the first and second undercuts in the distal head and the proximal neck may intersect with the third and fourth undercuts in the proximal head.

In yet another exemplary aspect, the present disclosure is directed to a kit for bone fixation and stabilization. The kit may comprise an intramedullary fixation device and insertion forceps. The intramedullary fixation device may comprise an arrowhead-shaped distal head having first, second, third, and fourth outwardly facing side surfaces forming a pyramidal shape. The first and third side surfaces may be opposed from each other and may form a first angle, and the second and fourth side surfaces may be opposed from each other and may form a second angle. Each of the first and third side surfaces may have a proximally projecting edge forming a tip of a barb. The barbs may be configured to engage tissue and inhibit movement of the distal head in a proximal direction, and wherein the second and fourth side surfaces lack barbs. The device may also comprise an arrowhead-shaped proximal head having fifth, sixth, seventh, and eighth outwardly facing side surfaces. The fifth and seventh side surfaces may be opposed from each other and may form a third angle, and the sixth and eighth side surfaces may be opposed from each other and may form a fourth angle. Each of the fifth and seventh side surfaces may have a distally projecting edge forming a tip of a barb. The barbs may be configured to engage tissue and inhibit movement of the proximal head in a distal direction. The sixth and eighth side surfaces may lack barbs. A cylindrical body extends between and connects the distal head and the proximal head. The cylindrical body may have a rigidity sufficient to withstand bending loading applied by the phalanges. The insertion forceps may be configured to securably grasp the intramedullary fixation device, and may include a first nose piece having a first recess formed therein. The first recess may be sized to receive a portion of the cylindrical body of the intramedullary fixation device. The insertion forceps may also include a second nose piece having a second recess formed therein. The second recess may be sized to receive a portion of the cylindrical body of the intramedullary fixation device. The first and second nose pieces may be cooperatively arranged to securely grip the cylindrical body of the intramedullary fixation device sufficiently to prevent rotation and axial displacement under normal insertion conditions.

In yet another exemplary aspect, the present disclosure is directed to a method comprising a step of grasping an intramedullary fixation device, introducing a proximal end of the device into an intramedullary canal of a first bone element, introducing a distal end of the device into an intramedullary canal of a second bone element, releasing the intramedullary fixation device, and pressing the first and second bone elements together.

In yet another exemplary aspect the present disclosure is directed to an intramedullary fixation device used in bone fixation and stabilization. The device comprises an arrowhead-shaped distal head comprising a distal end having a sharp distal point and also comprising distal first, second, and third outwardly facing side surfaces converging toward and intersecting at the distal point. The distal first outwardly facing surface may have a maximum width greater than a maximum width of the distal second outwardly facing surface. At least one of the distal first, second, and third outwardly facing surfaces may have a proximally projecting edge forming a tip of a barb configured to engage tissue and inhibit rotational movement and inhibit axial movement of the distal head in a proximal direction. The device also comprises an arrowhead-shaped proximal head comprising a proximal end having a sharp proximal point and also comprising proximal first, second, and third outwardly facing side surfaces converging toward and intersecting at the proximal point. The proximal first outwardly facing surface may have a maximum width greater than a maximum width of the proximal second outwardly facing surface. At least one of the proximal first, second, and third outwardly facing surfaces may have a distally projecting edge forming a tip of a barb configured to engage tissue and inhibit rotational movement and inhibit axial movement of the proximal head in a distal direction. A rigid body extends between and connects the distal head and the proximal head. The body may have a rigidity sufficient to withstand bending loading applied by the phalanges. In yet additional embodiments, the present disclosure is directed to a kit including the intramedullary fixation device. In yet additional embodiments, the present disclosure is directed to methods for implanting the intramedullary fixation device.

BRIEF DESCRIPTION OF THE DRAWINGS

FIG. 3 is an illustration of a side view of the exemplary intramedullary fixation device of FIG. 2 in accordance with one aspect of the present disclosure.

FIG. 3A is an illustration of a cross-sectional view along lines 3A in FIG. 3 through a head of the intramedullary fixation device of FIG. 3.

FIG. 4 is an illustration of another side view of the exemplary intramedullary fixation device of FIG. 2 rotated 90 degrees from the side view of FIG. 3.

FIG. 4A is an illustration of a cross-sectional view along lines 4A in FIG. 4 through a head of the intramedullary fixation device of FIG. 4.

FIGS. 7 and 7A are illustrations of an exemplary reamer surgical instrument usable for implantation of an intramedullary fixation device in accordance with one aspect of the present disclosure.

FIGS. 8 and 8A are illustrations of an exemplary broach surgical instrument usable for implantation of an intramedullary fixation device in accordance with one aspect of the present disclosure.

FIGS. 9 and 9A are illustrations of an exemplary insertion tool surgical instrument usable for implantation of an intramedullary fixation device in accordance with one aspect of the present disclosure.

DETAILED DESCRIPTION

Figure 1:
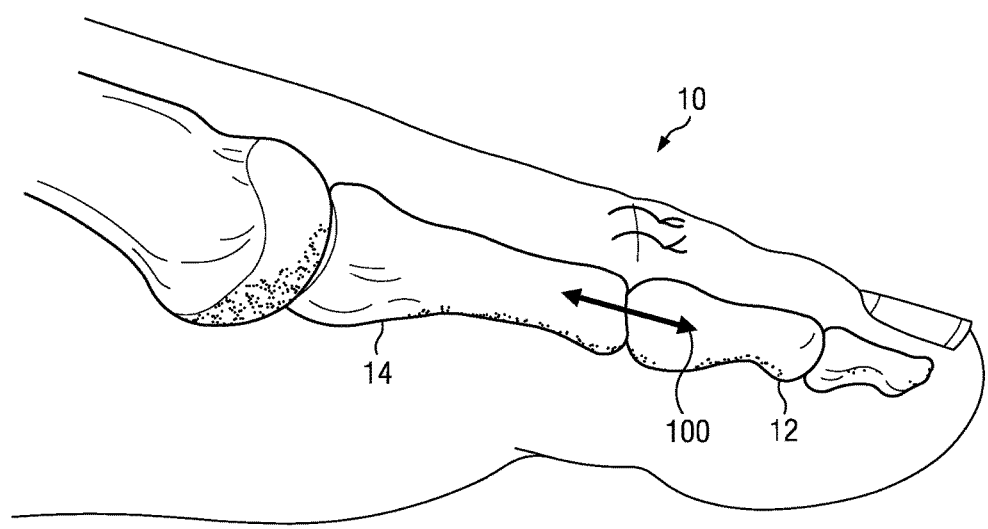
FIG. 1 is an illustration of an exemplary intramedullary fixation device disposed between and within adjacent phalanges of a toe of a patient in accordance with one aspect of the present disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present invention relates to an intramedullary fixation device used for bone fixation and stabilization of toes and fingers across fusion or fracture sites, and treat deformities, including for example, hammertoe deformities. The intramedullary fixation device includes a unique arrow design on both its proximal and distal ends. It is arranged to be completely intramedullary when implanted with no parts of the device exposed outside the skin. Further, it is arranged to resist the rotational and pull-out forces affecting the lesser toes. Its particular design shape may help it maintain the initial compression applied at insertion.

In addition, because of its convenient dual locking design, the intramedullary fixation device enables health care providers to perform implantation procedures faster and with less effort than prior techniques, such as those using external wires, such as K-wires. For example, it may require little or no bone removal when preparing for device insertion, potentially decreasing trauma and reducing recovery times. Further, the intramedullary fixation devices disclosed herein may remain permanently implanted. Accordingly, there is no need to schedule an additional procedure to remove this device as is necessary with temporary fixation devices, such as is required with K-wire fixation. As such, the intramedullary fixation devices disclosed herein may provide a more comfortable recovery, a lower incidence of infections, and the avoidance of that additional and often very uncomfortable procedure to remove the K-wire implant. Further, unlike the K-wire implants, the arrow designs at each end of the implant lock into bone reducing osseous movement or rotation.

FIG. 1 shows an exemplary toe 10 having an intermediate phalanx 12 and a proximal phalanx 14. In this example, the toe 10 has been surgically treated to correct a deformity such as hammertoe as discussed above. Accordingly, the toe includes an implanted intramedullary fixation device 100 disposed therein in accordance with an exemplary aspect of the present disclosure. In this example, the device 100 extends between and is implanted within the intermediate and proximal phalanges 12, 14. It is described in detail below.

Figure 2:
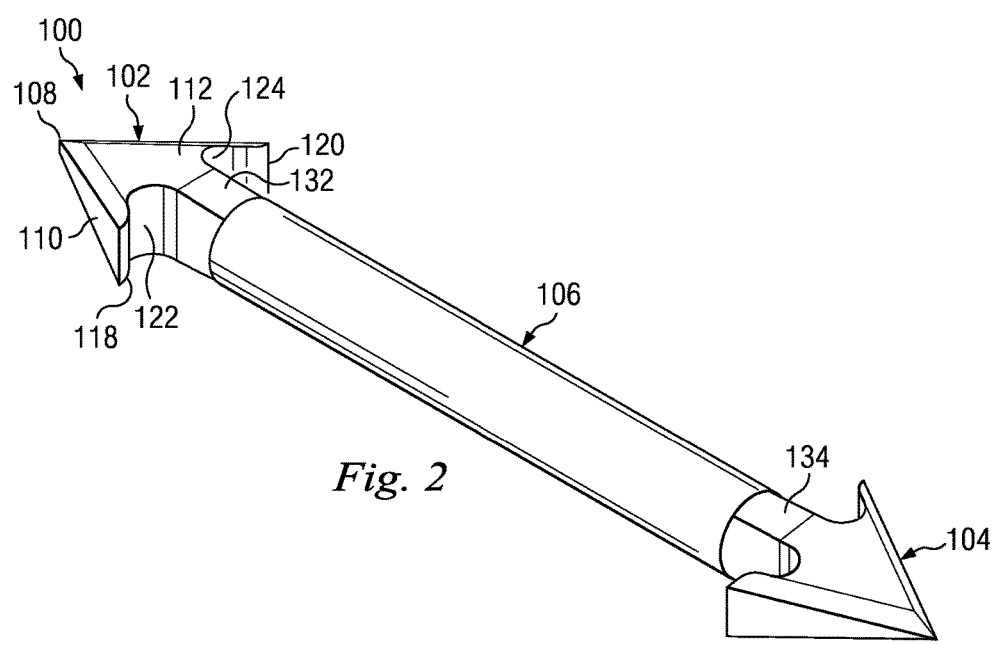
FIG. 2 is an illustration of the exemplary intramedullary fixation device of FIG. 1 in accordance with one aspect of the present disclosure.

FIGS. 2-4 show one exemplary embodiment of the device 100 of the present application. The device 100 is designed with a three-dimensionally configured arrow at each end and includes a first head 102, a second head 104, and a body 106 extending between the first and second heads 102, 104. As will become apparent from the below description, the individual components of the device 100 work in conjunction with one another to stabilize bone during arthrodesis procedures and across fractures. For reference, this disclosure refers to the first head 102 as a distal head and the second head 104 as the proximal head.

The distal head 102 is formed as a three dimensional arrowhead that is sized for placement in an intramedullary canal of a patient. It is configured so that edges of the arrowhead grasp the bone in the medullary canal as it is inserted, stabilizing the arthrodesis or fusion site during the osseous union. In this exemplary embodiment, the distal head 102 is formed as a distal end having a distal-most point 108. The distal-most point 108 leads the device 100 down the reamed or broached insertion channel to its final implantation site during insertion. In this example, the distal-most point 108 is a sharp point arranged to glide through tissue within the intramedullary canal to ease insertion. The sharp point 108 also may reduce trauma occurring due to a ripping or tearing effect that may occur with blunt or rounded tips. Other configurations of the arrowhead's tip may result in successful insertion based on preparation of the insertion site.

First, second, third, and fourth outer facing surfaces 110, 112, 114, 116 intersect at and extend from the distal most point 108 in the proximal direction, forming a four-sided pyramidal shape. Although shown as having four outer facing surfaces, some embodiments include greater or fewer outer facing side surfaces. In the example shown, opposing surfaces angle away from each other to define a leading angle. For example, the opposing first and third outer facing surfaces 110, 114 define an angle $\theta$ of the arrowhead shaped distal head 102. In some examples, the angle $\theta$ is in the range of about 30 degrees to about 90 degrees. In other examples, the angle $\theta$ is in the range of about 50 to 70 degrees, and in some embodiments, the angle is around 60 degrees. In a similar manner, the opposing second and fourth outer facing surfaces 112, 116 of the arrowhead shaped distal head 102 form an angle a. In the example shown, the angle $\alpha$ is smaller than the angle $\theta$. The angle a may be selected to be within the range of about 10-40 degrees, and in some embodiments, is in the range of about 15-25 degrees. In some examples, the angle a is about 19 degrees. The multiple angles described on the distal head may vary based on the size and strength of bone in which the device is to be implanted.

Because of the different angles between the opposing first and third surfaces 110, 114 and the opposing second and fourth surfaces 112, 116, the width of the distal head 102 differs from side to side. This is best seen in FIG. 3A, showing a cross-sectional view of the distal head 102 taken through the section 3A in FIG. 3. For example, FIG. 3A shows a width w1 of the first and third outer facing surfaces 110, 114 being less than a width w2 of the outer facing surfaces 112, 116. This differing width increases resistance to rotation that may occur if the device 100 were cylindrical or to a lesser extent substantially square, although such embodiments are contemplated. Further, the differing width may permit an implanted device to be removed, rotated 90 degrees and implanted again while still providing satisfactory anchoring.

Returning to FIG. 3, the distal head 102 may be sized to have a transverse width w3 greater than a longitudinal length L. The transverse width w3 may be sized in the range 2-6 mm and the longitudinal length L may be sized in the range of about 1.5-5.5 mm. In one example, the transverse width w3 is around 3.5 mm and the longitudinal length L is about 3 mm. Other sizes however, both larger and smaller, are contemplated, and in one example, the width and the length are substantially equal.

In the example shown, the distal head 102 includes two proximally projecting barbs 118, 120. These barbs are configured to engage tissue within the intramedullary canal and resist movement and migration and/or axial displacement within the canal once they have been inserted into the canal. As can be seen, these barbs 118, 120 are formed by edges of respective outer facing surfaces 110, 114 and because of the pyramidal shape of the distal head, the edges lie in substantially parallel lines.

Inner surfaces of the barbs 118, 120 are formed by first and second undercuts 122, 124 disposed respectively between tips of the barbs 118, 120 and the body 106. In this example, the undercuts are formed so that they cut into the body in a direction and at a location distal of proximal tips of the barbs 118, 120. This is shown also in the cross-sectional view of FIG. 4A, taken along lines 4A in FIG. 4. In this example, the undercuts 122, 124 are formed by arcing surfaces. Because of the curvature, the arcing surfaces have a distal peak that is distal of the tips of the barbs 118, 120 themselves. The undercut surfaces 122, 124 merge with the body 106 to provide greater pull-out resistance. The shape shown, with its arcing surfaces, may expose a larger surface area to cancellous bone, thereby increasing the resistance to the pull-out forces as compared to a straight surface. The undercuts themselves provides space that accommodates bony ingrowth to provide additional pull-out resistance and further stabilize the implant during healing and fusion. While in the example shown, the barbs are substantially rigid or inflexible, in other embodiments, the undercut may also serve to allow the barbs to flex when the implant becomes lodged in hard cortical bone. In some embodiments, the undercuts are formed with surface profiles or shapes other than proximal arcs. For example, some embodiments have undercuts that are formed with substantially flat surfaces disposed distal of tips of the barbs 118, 120. These may be transverse to the longitudinal direction of the device 100. Other embodiments have undercuts that project deeply into the distal head 102, substantially parallel to the angled outer facing surfaces 110, 114. These may be suitable when less pull-out strength is needed. Because there is only one barb 118, 120 along each side of the device 100, insertion may result in less tissue disruption than an arrow having multiple barbs or having a several points of equal maximum width. As a result of lower trauma, the tissue itself may be more intact for securing the barbs and resisting removal or axial displacement from the intramedullary canal.

The body 106 extends between and connects the distal head 102 and the proximal head 104. It is a one-piece rigid element structurally configured to withstand loading applied across the joint or fracture being supported. It includes a main body portion 130 and necks 132, 134 at either end leading to the distal and proximal heads 102, 104. As can be seen, the main body portion 130 has a diameter larger than that of the necks 132, 134. For the reasons explained below, the larger body portion 130 may be easier to grasp and secure because it has a larger perimeter surface area, while the necks 132, 134 may be sized to permit additional tissue placement and tissue growth immediately adjacent the undercut surfaces 122, 124 of the distal and proximal heads 102, 104. This may result in more secure and lasting anchoring. Thus, this structural arrangement may provide space for extra tissue to grow behind the arrowhead to aid in fixation, while still providing a large gripping surface on the body 106. In the embodiment shown, the diameter of the main body 130 is in the range of about 1-3 mm, and preferably has a diameter around 1.5 mm. Both larger and smaller diameters are contemplated. In the example shown, the main body 130 is cylindrically shaped, which provides consistent strength characteristics through the length of the implant. Further, the diameter is substantially consistent along its length in order to permit the implant to be gripped with insertion tools at any point along the main body in order to best fit the anatomic variations of the phalanges. Because the main body has a round profile, the body may be gripped with an insertion tool at any desired rotational orientation relative to the tool, permitting the health care provider to orient and penetrate the desired bone location. The length of the body 106 is selected so that the opposing distal and proximal heads lie at the desired location within the phalanx when inserted in the bone. Accordingly, without limitation, in some embodiments, the length of the device 100 is within a range of about 10-50 mm, and the body 106 has a length of 7-44 mm. In one example, the length of the body 106 is in the range of about 7-15 mm, and in one example, has a length of about 13 mm. Both larger and smaller bodies are contemplated.

Still referring to these figures, the second and fourth outer facing surfaces 112, 116 are angled and intersect with the body 106 at the neck 132. In some examples, the second and fourth outer facing surfaces 112, 114 may smoothly transition to the neck and in other examples, the second and fourth outer facing surfaces 112, 114 meet the neck 132 at an intersecting angle. In some examples, the neck 132 is formed with a rounded perimeter having a diameter substantially similar to the distance between the proximal ends of the second and fourth outer facing surfaces 112, 114.

In the exemplary embodiment shown, each of the edges joining adjacent outer facing surfaces 110, 112, 114, 116 is chamfered or rounded, resulting in less sharp edges. This may be best seen in the cross-sectional view shown in FIG. 3A. In the example shown, the distal head 102 includes chamfers 136 formed at 45 degree angles relative to the outer facing surfaces 110, 112, 114, and 116. Other embodiments however, include chamfers at other angles or rounds with a radius that provides smooth transition from one outer facing surface to another. As such, in some examples, tissue may be more likely to be deflected and pushed aside during advancement of the distal head into the tissue than to be cut by what might otherwise be sharp 90 degree edges between adjacent outer facing surfaces 110, 112, 114, 116. This may result in better purchase because tissue may be better left intact during insertion of the device 100.

The second or proximal head 104 is, in the example shown, substantially similar to the distal head 102, but extends from the body 106 in the opposing direction. For clarity and to reduce duplication, the description above of the proximal head is not repeated here with the understanding that the description above applies equally to the proximal head 104. The distal and proximal heads, due to their shape and opposing configuration, resist migration, pullout, and rotation.

The proximal and distal heads 102, 104 and the body 106 are, in the example shown, equivalent to one another having substantially the same size and configuration. In some examples however, the size or configuration of the distal and proximal heads are different. For example, the angle α between the second and fourth outer facing surfaces on the proximal head may be larger or smaller than the angle between the second and fourth outer facing surfaces on the distal head. Likewise, the angle θ between the first and third outer facing surfaces on the proximal head may be larger or smaller than the angle between the second and fourth outer facing surfaces on the distal head. In some examples, the distal and proximal heads are merely scaled in size relative to each other. In one example, the transverse widths $w_3$ of the distal head and the proximal head are substantially equally sized at about 3.5 mm and the longitudinal lengths L are equally sized at about 3.0 mm. In another example, the transverse width $w_3$ of the proximal head is about 3.5 mm, and the transverse width of the distal head is selected as one of about 2.0 mm, about 2.5 mm, and about 3.0 mm. In another example, the transverse width of the proximal head is selected to be about 4.0 mm, and the transverse width of the distal head is selected to be about one of about 2.0 mm, about 3.0 mm, and about 3.5 mm. The size of the distal and proximal heads may be selected based on their intended utility, including whether the device is intended for implantation in a toe phalanx or a finger phalanx or across a fracture, for example. Because not all medullary canals have the same diameter, a health care provider may select an implant to achieve a desired fit. For example, a health care provider may accommodate situations where the proximal phalanx has a larger medullary canal than the medullary canal of the intermediate phalanx. Although described as though the proximal head is larger than the distal head, in some examples the distal head may be sized larger than the proximal head by any of the dimensions discussed above. Although particular maximum widths are provided as examples here, the sizes may be dimensioned larger or smaller than those indicated, and sizes may be offered in any desired size increment. Further, the angles may differ based on the size or diameter of bones to be treated. Accordingly, the device 100 may be sized to fit a wide range of anatomies, as well as different joints of the phalanges.

The device 100 may be sterilized and may be formed of biocompatible materials, including stainless steels and titanium as well as non-metallic materials, such as composites, polymers, and bioresorbables. In one example the device is formed of 316L (F138) stainless steel. In some examples, the device 100 is manufactured from a solid bar by a mechanical metal removal process, such as machining. After machining, the product may be passivated per ASTM A967-96 to remove any surface contaminants. It may then be electropolished to improve the surface finish and edge finish and may be laser marked for identification. Some designs may lend themselves to a metal injection molding process.

Figure 5:
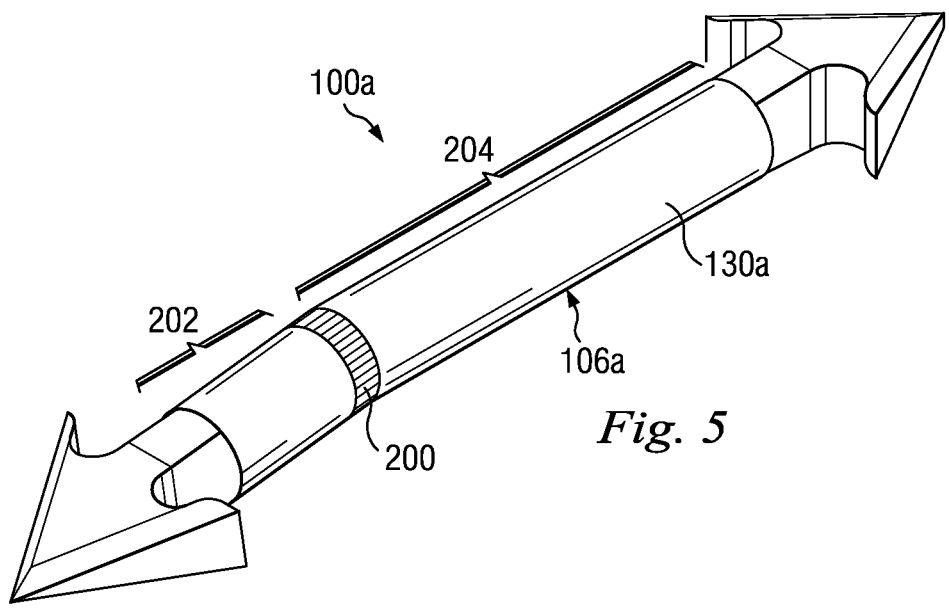
FIG. 5 is an illustration of another exemplary intramedullary fixation device in accordance with one aspect of the present disclosure.

FIG. 5 shows another embodiment of the device 100. For reference the device in FIG. 5 will be referenced by the numeral 100a. Since many of the features are the same as the device 100 in FIGS. 2-4, only the differences will be described in detail. The device 100a includes a body 106a formed of a main body portion 130a having a plantar grade bend 200. In this example, the bend 200 is a 10 degree plantar grade bend. Different embodiments include a bend that may be selected in the range of about 5-25 degrees. In some examples, the bend is selected to be about a 15 degree bend, while yet other embodiments the bend is selected to be about a 5 degree bend. The bend divides the body portion 130a into a first portion 202 and a second portion 204. The first and second portions 202, 204 respectively define first and second longitudinal axes that intersect at the bend 200. In some examples, the bend 200 is disposed at a location within a range of about 40-80% of the length of the body portion 130a. In some examples, the bend is within a range of about 50-70% of the length of the body portion 130a. In some examples, the bend is at about 60% of the length of the body portion 130a. In other examples however, the bend 200 is disposed at other locations. Although shown with a 10 degree bend, other embodiments include a bend angled within a range of about 5-30 degrees, and in some examples, angled within a range of about 7-15 degrees. In some examples, the longer segment is particularly suited for accommodating the proximal phalanx and the shorter segment is particularly suited for accommodating the intermediate segment. Like the embodiments described above, the device 100a is formed of a single solid, monolith material. Accordingly, there are no seams, welds, joints, or other stress introducers. Whether to use a straight or bent configuration will depend on the deformity. The bent device 100a provides a similar bend to the bone structure at the fusion/fracture site.

Figure 6:
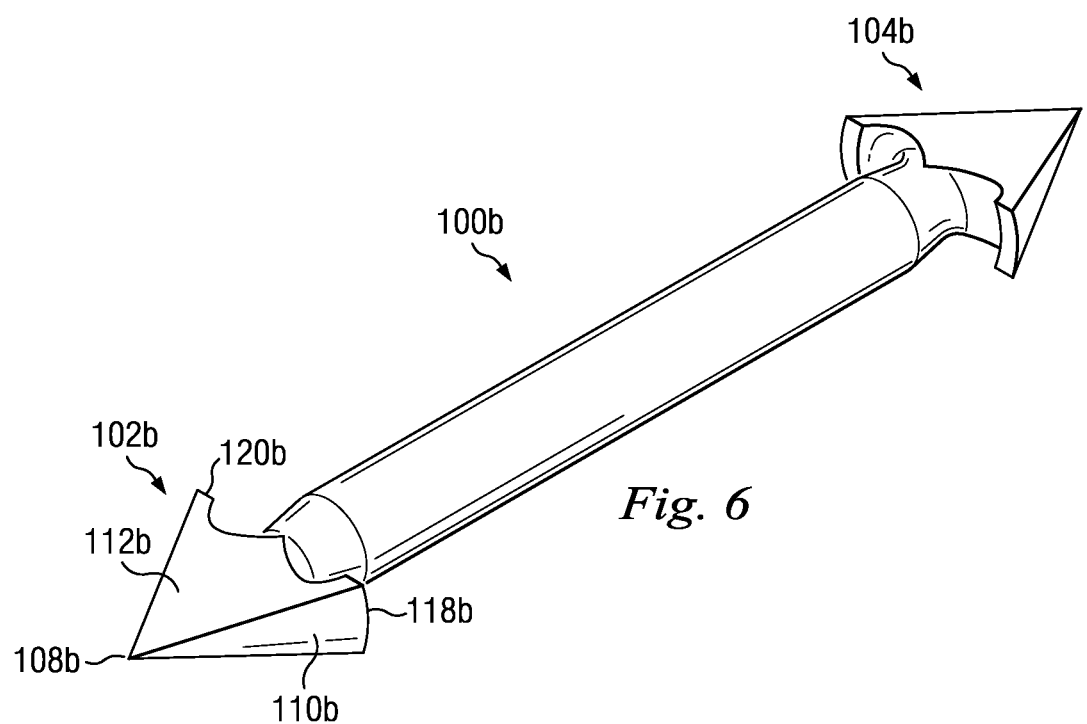
FIG. 6 is an illustration of another exemplary intramedullary fixation device in accordance with one aspect of the present disclosure.

FIG. 6 shows another embodiment of the device 100. For reference the device in FIG. 6 will be referenced by the numeral 100b. Since many of the features are the same as the device 100 in FIGS. 2-4, only differences will be described in detail with the understanding that other details and much of the description above applies equally to the device 100b. The device 100b includes first and second heads 102b, 104b. Like the heads described with reference to FIGS. 2-4, the first and second heads 102, 104 are three dimensional arrowheads.

For convenience, only the first head 102b, referred to as the distal head, will be described in detail. The distal head 102b includes a sharp distal-most point 108b. First, second, third, and fourth outer facing surfaces extend from the distal most point 108b in the proximal direction, forming a pyramidal shape. In FIG. 6, only two outer facing surfaces 110b, 112b of the four outer facing surfaces are shown. It is understood that the opposing, non-visible surfaces are substantially identical to the surfaces 110b, 112b shown. In this embodiment however, the outer facing surface 110b and its opposing surface are not entirely planar, but are shaped slightly convex with a large radius such that the outer facing surface 110b arcs between the adjacent substantially planar side surface 112b and the outer facing surface opposing surface 112b. Because of this, the barbs 118b, 120c also include a slightly arched or rounded shape. Here, the radius of the arc is sized larger than a width of or diameter of the implant itself.

Intersections of adjacent outer facing surfaces form edges that, in this example, are not chamfered or rounded. However, because of the slightly convex surface shape of at least two of the outer facing surfaces, the edges in this example still do not form true right angles, but form angles less than 90 degrees. It should be noted that 90 degree angles are also contemplated.

FIGS. 7-9 show surgical instruments that may be used to implant the devices described above. FIGS. 7 and 7A show a reamer 300, FIGS. 8 and 8A show a broach 320, and FIGS. 9 and 9A show insertion forceps 340.

Turning first to FIG. 7, the reamer 300 may be formed of a length of stainless steel wire having a diameter selected to penetrate and fit within and create pilot holes in intramedullary canals of toe or finger phalanges without removing bone. In one embodiment, the reamer 300 may have a diameter of about 1.6 mm. The reamer 300 may include a smooth trocar tip 302 configured to create a pilot hole without removing bone. In some examples, the reamer 300 includes markings 304 that serve as a depth gauge when reaming intramedullary canals. FIG. 7A shows the tip 302 in greater detail with laser markings 304 spaced, for example, at increments of 5 mm. Other embodiments include markings at different intervals, while yet other embodiments include a single marking indicating a pre-established depth. Some embodiments do not include any markings at all and the surgeon estimates the depth of the reamer 300.

FIG. 8 shows the broach 320 in greater detail. The broach is sized and configured for insertion into the pilot holes created by the reamer 300 to prepare the pilot hole for insertion of the device 100. Here, the broach 320 includes a handle 322 and a broach tool 324. In some examples, the diameter of the broach tool 324 is double the diameter of the reamer 300. The broach tool diameter may be, for example, selected to be within a range of about 1.5-5.0 mm. In other examples, the diameter is selected to be within a range of about 2.5-3.5 mm. In some examples, the broach tool 324 is sized with a diameter of about 3.2 mm. Diameters larger and smaller are contemplated. In the example shown, the broach tool 324 includes a pointed conical tip 326 having an angle that matches the greatest angle of the distal and proximal heads 102, 104 of the device 100. For example, if the device 100 includes first and third outwardly facing surfaces 110, 114 forming an angle θ of, for example, 60 degrees, then the angle formed by sides of the conical tip 326 of the broach tool 324 may also be angled at 60 degrees. In other examples, the tip angle may be vary from the greatest angle of the distal and proximal heads, and may, for example, be selected to match the angle a formed by the second and fourth outer facing surfaces 112, 116. In other embodiments, the tip angle is larger or smaller than the angles of the outer facings surfaces.

FIG. 8A shows a part of the broach tool 324 in greater detail. In some examples, the broach tool 324 includes markings 328 that serve as a depth gauge when enlarging the pilot hole in the intramedullary canals. In this example, the laser markings 328 are spaced, for example, at increments of 5 mm. Other embodiments include markings at different intervals, while yet other embodiments include a single marking indicating a pre-established depth. Some embodiments do not include any markings at all and the surgeon estimates the depth of the broach tool 324. In the example shown, the broach tool 324 includes a sharp point and blade edges in order to penetrate the hard subcondral bone lying just beneath the cartilagenous surfaces. In a similar way, the sharp point and blades facilitate penetration of hard sclerotic bone. The broach shaft profile then rapidly increases in diameter to a profile more closely approximating that of the three dimensional arrow in order to facilitate the insertion of the definitive implant. The broach width is sized in relation to the implant to provide the proper balance between ease of insertion and resistance to rotational and pull-out forces. In some examples, this value ranges between 70% and 85% of the implant width and in one embodiment is about 77% of the implant width.

FIG. 9 shows the insertion forceps 340 in greater detail. The insertion forceps 340 have a grasping end 342 formed of first and second nose pieces 344, 346 pivotably connected in a manner to close upon and grip the device 100 and have a gripping end 348 with a locking mechanism 350 that secures the forceps 310 in a clamping position. As shown in FIG. 9A, each nose piece 344, 346 includes a transverse semicircular recess 352, 354 formed therein, aligned with each other when the nose pieces 344, 346 are adjacent each other. The recesses 352, 354 are formed in a manner permitting frictional engagement about the body 106 of the device 100 to secure it against both rotational and axial displacement relative to the insertion forceps 340. In the example shown, the recesses are round to match the cylindrical shape of the body 106 of the device 100. Because of the cylindrical shape of the body 106, the insertion forceps 340 can be oriented a full 360° in relation to the arrowhead tip to accommodate surgeon preference or anatomical variations. The radius dimension is determined based on the diameter of the body 106 in order to properly mate with the body 106. In some examples, the diameter formed by the two opposing recesses is within a range of about 5-15% smaller than the diameter of the body 106, thereby ensuring a secure grip on the device 100. In one example, the diameter of the body 106 is about 1.50 mm, then the recesses 352, 354 may each have a radius of 0.70 mm, together forming a diameter of 1.4 mm. In other examples, the radius is sized to substantially match that of the body 106. Both larger and smaller recesses are contemplated. It is to be noted that the larger the diameter of the body 106, the greater the surface area that is in contact with the insertion forceps, increasing frictional resistance. Therefore, a relatively large diameter of the body 106 may be desirable, resulting in a matching relatively large diameter of the recesses 352, 354. During use, the insertion forceps 340 can be used to create a positive stop that prevents the implant from inadvertently being inserted to a greater depth than desired. In addition, it can create a visual representation of the depth to which the surgeon desires to place the implant. Further, it is configured in a manner providing a safe surface upon which to strike should the implant need additional force to progress down the reamed intramedullary canal.

In some examples, the device 100 is provided as a kit with one or more of the instruments described above. One exemplary kit includes a device 100 as described above, with the reamer 300, the broach 320, and the insertion forceps 340. Another exemplary kit includes both the device 100 and the device 100a, along with the reamer 300, the broach 320, and the insertion forceps 340. Other exemplary kits include only one of the instruments with one or more of the devices 100, 100a. In one example, the kit includes a sterilized device 100, 100a and sterilized, single use instruments including one or more of the reamer 300, the broach 320, and the insertion forceps 340. In another example, the kit includes a sterilized device 100, 100a, and multiple use instruments including one or more of the reamer 300, the broach 320, and the insertion forceps 340. Some kit embodiments include a plurality of devices 100, 100a, with the instruments. In one example, a kit includes six devices and one set of instruments. In one example, the instruments are provided in an autoclavable tray (not shown) for sterilization. Other kits and arrangements are also contemplated.

Figure 10:
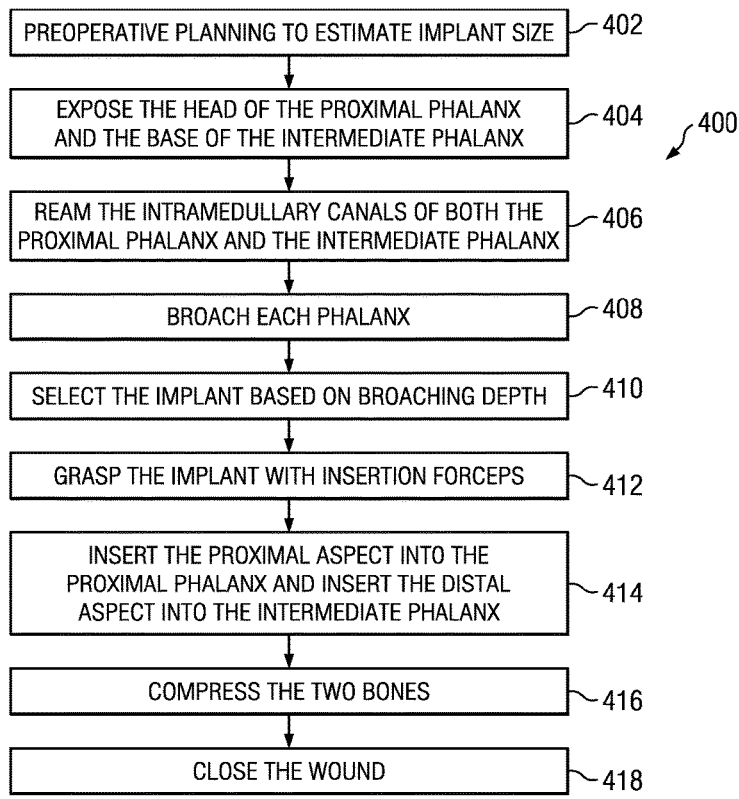
FIG. 10 is a flow chart of an exemplary surgical method of implanting an intramedullary fixation device in accordance with one aspect of the present disclosure.

FIG. 10 is a flow chart describing an exemplary surgical method 400 for implanting the device 100 using the instruments disclosed herein. As becomes apparent from the description below, the arrowhead configuration of both the distal and proximal heads 102, 104 captures bone on both sides of the fusion or fracture site, and may provide internal stability. This is accomplished by pressing and locking the distal and proximal heads 102, 104 into the surrounding bone. The body 106 of the device 100 extends from each head (proximal and distal) and is the portion of the implant that crosses or spans the fusion or fracture site.

The method begins at a step 402 where a health care provider estimates the diameter and length of the implant based upon pre-operative planning. In some examples, this is accomplished by taking and examining pre-op radiographs to estimate the inner diameter of the intramedullary canals of the affected phalanges at the location where the distal and proximal heads of the device 100 are expected to engage. In one example, this includes measuring with a ruler the inner diameter at the point of engagement in the bone. In some examples, the health care provider calculates the diameter by overlaying an image of the implant upon the patient's radiograph taking into account radiograph magnification. The device may be selected so that the inner diameter of the intramedullary canal is at least the same width as the distal or proximal head. Accordingly, in some examples, to achieve an effective fit, the health care provider selects a device with different sized heads. This may increase the likelihood of achieving proper purchase, may ease insertion, and may mitigate impingement of the arrow barbs upon the cortices. The step of selecting the implant based on size may also include estimating the proper length of the device 100 that will engage each phalanx at the desired point of contact. This projected length will also enable the health care provider to approximate the broaching depth for each phalanx.

At a step 404, the health care provider exposes the head of the proximal phalanx and the proximal end of the intermediate phalanx. This may be accomplished by creating an incision over the point of implantation and dissecting through the skin and subcutaneous tissues to expose the head of the proximal phalanx. Tissue may then be removed from the proximal end of the intermediate phalanx. This may include freeing the base of the phalanx from the plantar plate if the health care provider cannot distract the toe enough to place it on the distal head of the implant. Once properly exposed, the health care provider resects the head of the proximal phalanx and the base of the intermediate phalanx.

At a step 406, the health care provider creates pilot holes down intramedullary canals of both the proximal and intermediate phalanx using the reamer 300. This may include observing laser marks to estimate depth of the pilot hole so that the depth corresponds to the depth determined when selecting the implant based on size in step 402. Alternatively, a pre-drill with K-wire or a hand drill may be performed to form the pilot holes.

At a step 408, the health care provider broaches the pilot hole in each phalanx with the broach 320. This increases the diameter of the pilot hole to prepare it for receiving the device 100. Similar to step 408, this may include observing laser marks to estimate depth of the broached hole so that the depth corresponds to the depth determined when selecting the implant based on size in step 402. Broaching the hole may conserve bone by compacting the cancellous bone of the phalanx to engage the distal and proximal heads of the device 100 upon insertion. In some examples, as indicated at step 410, the health care provider notes the broach depth, and reevaluates, or evaluates for the first time, the length of the device needed to achieve a desired fit in the broached pilot hole.

Since the device 100 shown herein is a one-piece device formed of substantially rigid material, it does not require special pre-operative handling. For example, because it does not require deflection for anchoring as do some devices made of shape memory alloys, the device 100 may be maintained at room temperature.

At a step 412, the health care provider grasps the device 100 using the insertion forceps 340. This may include fitting the body 106 in the recesses 352, 354 of the insertion forceps 340 and securing the grip with the locking mechanism 350. Further, it may include grasping the device 100 at a distance from an end that corresponds to the broaching depth of the proximal phalanx. At a step 414, the health care provider axially inserts the device 100 into the proximal phalanx, securing it into the intramedullary canal. The insertion forceps may be used as a positive stop that prevents the implant from inadvertently being inserted to a greater depth than desired. In addition, the surfaces on the heads of the device 100 help the implant stay within the broached canal, while the taper helps reduce the likelihood of it catching on cancellous bone. Keeping the insertion forceps 340 attached to the device 100, the surgeon then grasps the digit of the toe with the distal portion of bone and places the digit over the distal aspect of the device 100 into the broached hole prepared in the intermediate phalanx, locking the device 100 into the intramedullary canal. This is then compressed against the insertion tool 340. With both ends of the device 100 in the respective, adjacent phalanges, the insertion forceps 340 may be removed from the device 100.

At a step 416, the health care provider then grasps and compresses the two phalanges together to advance the proximal and distal ends of the device 100 deeper into both intramedullary canals to a final, locked position. Thus, the device 100 is completely intramedullary. At a step 418, the wound is closed using the surgeon's preferred technique. In some examples, either before or after closing the wound, the final position of the device 100 may be evaluated radiographically to ensure that the phalanges are in close contact without gapping. Since the device 100 may be a single-use bone fixation device designed to be permanently implanted in the medullary canal of the bone, follow-up procedures and surgeries may be unnecessary. Although described with reference to the device 100, it would be apparent that the same method would be employed with any of the devices disclosed herein.

Figure 11:
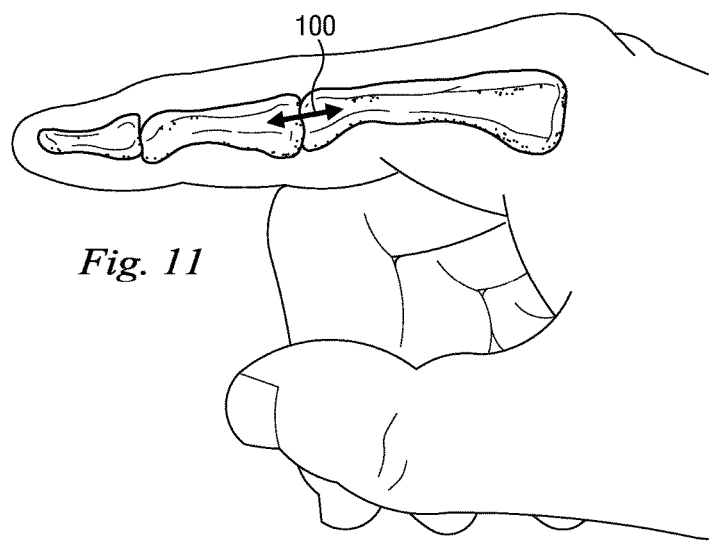
FIG. 11 is an illustration of an exemplary intramedullary fixation device disposed between and within adjacent phalanges of a finger of a patient in accordance with one aspect of the present disclosure.

As indicated above, the exemplary device 100 may be used for treatments other than hammertoe, and in some examples, may be used to treat conditions in the fingers of a hand, or alternatively may be used to treat bone fractures. FIG. 11 is one example showing the device 100 implanted within phalanges of the hand. The device 100 may be implanted in a manner substantially similar to that described above. In addition, removal of the device may be relatively easier than prior, conventional devices. For example, to remove the device, the cylindrical main body may be first cut, and then a cannulated drill may be fit over the cylindrical main body and drilled over to remove bony on-growth from the cylindrical body so that the arrowhead tip can be removed without tearing the bone. This may prevent the health care provider from having to cut the cortical bone in order to remove the implant. Accordingly, the cylindrical shape of the main body may help reduce a chance of compromising cortical bone during revision surgeries. Uses of the device 100 may include but are not limited to hand surgery, orthopedic surgery, plastic surgery, and podiatric surgery. In addition, the implant may be inserted in a variety of angles that differ from its intended position in medullary bone. In some examples, the implant may also be placed through cortical bone and tendon of the hand or foot.

In some examples, the device 100 is machined from a single piece of 316L stainless steel, making it a weld-less, single monolith structure. Various lengths may be provided to meet patient sizing restrictions. The overall lengths of the device 100 may be in the range of 10 mm to 40 mm, while some lengths are within the range of 15 mm to 25 mm. When the device 10 is formed of a single piece of metal, potential stress-risers occurring from welds or adhesives are eliminated and there is no need to assemble intra-operatively. Further, the material and size are selected so that the device has bending and fatigue characteristics able to endure the forces exerted on the lesser toes.

In some examples, the arrowheads may be reconfigured at different positions to one another and may obtain the same stability to the arthrodesis/fracture site. For example, some embodiments have a proximal arrow vertical to the shaft or a distal arrow horizontal to the shaft. The same can be said for different angle increments to each arrow.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An intramedullary fixation device, comprising:
an arrowhead-shaped distal head comprising a distal end having a tip, the distal head further comprising first, second, third, and fourth outwardly facing side surfaces forming a pyramidal shape, the first and third side surfaces being opposed from each other and forming a first angle, and the second and fourth side surfaces being opposed from each other and forming a second angle, the second angle being different than the first angle, each of the first and third side surfaces having a proximal edge configured to engage tissue and inhibit rotational movement and inhibit axial movement of the distal head in a proximal direction, the distal head being sized to fit within an intramedullary canal of a distal portion of a first bone;
an arrowhead-shaped proximal head comprising a proximal end having a tip, the proximal head being sized to fit within an intramedullary canal of a proximal portion of a second bone; and
a rigid body connecting the distal head and the proximal head, the rigid body comprising a central portion, a distal neck portion connecting the rigid body to the distal head, and a proximal neck portion connecting the rigid body to the proximal head, the distal and proximal neck portions having a cross-sectional area smaller than a cross-section area of the central portion.

2. The intramedullary fixation device of claim 1, wherein the proximal head further comprises fifth, sixth, seventh, and eighth outwardly facing side surfaces, the fifth and seventh side surfaces being opposed from each other and forming a third angle, and the sixth and eighth side surfaces being opposed from each other and forming a fourth angle, the third angle being different than the fourth angle, each of the fifth and seventh side surfaces having a distal edge configured to engage tissue and inhibit rotational movement and inhibit axial movement of the proximal head in a distal direction.

3. The intramedullary fixation device of claim 2, wherein the first angle is larger than the third angle.

4. The intramedullary fixation device of claim 1, wherein the first angle is larger than the second angle.

5. The intramedullary fixation device of claim 1, wherein the second and fourth side surfaces include proximal ends that relatively smoothly transition to the rigid body.

6. The intramedullary fixation device of claim 1, wherein the second and fourth surfaces intersect with a surface of the distal neck portion, and wherein the first and third surfaces do not intersect with a surface of the distal neck portion.

7. The intramedullary fixation device of claim 1, further comprising chamfered edges between adjacent surfaces of the first, second, third, and fourth outwardly facing side surfaces of the distal head.

8. The intramedullary fixation device of claim 1, wherein the rigid body comprises a first portion and a second portion, the first portion being angled relative to the second portion.

9. The intramedullary fixation device of claim 8, wherein the first portion has a length less than a length of the second portion.

10. The intramedullary fixation device of claim 8, wherein the first portion is angled about 10 degrees relative to the second portion.

11. The intramedullary fixation device of claim 1, wherein the first, second, third, and fourth outwardly facing side surfaces of the distal head are planar surfaces.

12. An intramedullary fixation device, comprising:
an arrowhead-shaped proximal head comprising a proximal end having a tip, the proximal head further comprising first, second, third, and fourth outwardly facing side surfaces forming a pyramidal shape, the first and third side surfaces being opposed from each other and forming a first angle, and the second and fourth side surfaces being opposed from each other and forming a second angle, the second angle being different than the first angle, each of the first and third side surfaces having a proximal edge configured to engage tissue and inhibit rotational movement and inhibit axial movement of the proximal head in a proximal direction, the proximal head being sized to fit within an intramedullary canal of a proximal portion of a first bone;
an arrowhead-shaped distal head comprising a distal end having a tip, the distal head being sized to fit within an intramedullary canal of a distal portion of a second bone; and
a rigid body extending between the proximal head and the distal head, the rigid body comprising an intermediate portion, a proximal neck portion connecting the rigid body to the proximal head, and a distal neck portion connecting the rigid body to the distal head, the proximal and distal neck portions having a cross-sectional area smaller than a cross-section area of the intermediate portion.

13. The intramedullary fixation device of claim 12, wherein the distal head further comprises fifth, sixth, seventh, and eighth outwardly facing side surfaces, the fifth and seventh side surfaces being opposed from each other and forming a third angle, and the sixth and eighth side surfaces being opposed from each other and forming a fourth angle, the third angle being different than the fourth angle, each of the fifth and seventh side surfaces having a distal edge configured to engage tissue and inhibit rotational movement and inhibit axial movement of the distal head in a distal direction.

14. The intramedullary fixation device of claim 13, wherein the first angle is larger than the third angle.

15. The intramedullary fixation device of claim 12, wherein the first angle is larger than the second angle.

16. The intramedullary fixation device of claim 12, wherein the second and fourth side surfaces include proximal ends that transition to the rigid body.

17. The intramedullary fixation device of claim 12, wherein the second and fourth surfaces intersect with a surface of the proximal neck portion, and wherein the first and third surfaces do not intersect with the surface of the proximal neck portion.

18. The intramedullary fixation device of claim 12, further comprising chamfered edges between adjacent surfaces of the first, second, third, and fourth outwardly facing side surfaces of the proximal head.

19. The intramedullary fixation device of claim 12, wherein the rigid body comprises a first portion and a second portion, the first portion being angled relative to the second portion, and the first portion has a length less than a length of the second portion.

20. The intramedullary fixation device of claim 12, wherein the first, second, third, and fourth outwardly facing side surfaces of the proximal head are planar surfaces.

* * * * *